(12) United States Patent
Tsurimoto et al.

(10) Patent No.: US 10,980,543 B2
(45) Date of Patent: Apr. 20, 2021

(54) STAPLER

(71) Applicant: OLYMPUS CORPORATION, Tokyo (JP)

(72) Inventors: Keisuke Tsurimoto, Tokyo (JP); Masatoshi Iida, Tokyo (JP); Kayuri Kimura, Saitama (JP)

(73) Assignee: OLYMPUS CORPORATION, Tokyo (JP)

(*) Notice: Subject to any disclaimer, the term of this patent is extended or adjusted under 35 U.S.C. 154(b) by 224 days.

(21) Appl. No.: 16/297,821

(22) Filed: Mar. 11, 2019

(65) Prior Publication Data
US 2019/0200999 A1 Jul. 4, 2019

Related U.S. Application Data

(63) Continuation of application No. PCT/JP2016/084074, filed on Nov. 17, 2016.

(51) Int. Cl.
*A61B 17/072* (2006.01)
*A61B 17/115* (2006.01)
(Continued)

(52) U.S. Cl.
CPC ........ *A61B 17/1155* (2013.01); *A61B 17/072* (2013.01); *A61B 17/07207* (2013.01);
(Continued)

(58) Field of Classification Search
CPC ................ A61B 17/068; A61B 17/072; A61B 17/07207; A61B 17/115; A61B 17/1155;
(Continued)

(56) References Cited

U.S. PATENT DOCUMENTS 4,310,115 A 1/1982 Inoue
4,475,679 A * 10/1984 Fleury, Jr. ............ A61B 17/072
206/339
(Continued)

FOREIGN PATENT DOCUMENTS

EP 2174599 A2 4/2010
EP 3058880 A1 8/2016
(Continued)

OTHER PUBLICATIONS

International Search Report dated Feb. 7, 2017 issued in PCT/JP2016/084074.

*Primary Examiner* — Scott A Smith
(74) *Attorney, Agent, or Firm* — Scully, Scott, Murphy & Presser, P.C.

(57) ABSTRACT

A stapler according to the present invention is provided with: a holder provided with an accommodating portion that accommodates a plurality of staples with tips thereof, which pass through a suturing target, directed in one direction; a plurality of pushers that push out the staples accommodated in the accommodating portion in accordance with a plurality of groups thereof; an anvil that presses and deforms the staples pushed out from the accommodating portion by the pushers; driving-force transmitting mechanisms that are respectively connected to the individual pushers, in which the movement thereof in directions other than the directions in which the staples are pushed out is restricted at the individual connection portions, and that transmit driving forces that move the individual pushers toward the anvil.

20 Claims, 12 Drawing Sheets

(51) Int. Cl.
*A61B 17/00* (2006.01)
*A61B 17/068* (2006.01)
*A61B 17/29* (2006.01)

(52) U.S. Cl.
CPC ... *A61B 17/068* (2013.01); *A61B 2017/00017* (2013.01); *A61B 2017/00398* (2013.01); *A61B 2017/00734* (2013.01); *A61B 2017/07214* (2013.01); *A61B 2017/07235* (2013.01); *A61B 2017/07257* (2013.01); *A61B 2017/07278* (2013.01); *A61B 2017/07285* (2013.01); *A61B 2017/2927* (2013.01)

(58) Field of Classification Search
CPC ...... A61B 17/0682; A61B 2017/07214; A61B 2017/07235; A61B 2017/07271; A61B 2017/07278; A61B 2017/2927; A61B 2017/2933; A61B 2017/2943
USPC .. 227/19, 175.1, 176.1, 175.2, 178.1, 180.1; 606/1, 139, 153, 219
See application file for complete search history.

(56) References Cited

U.S. PATENT DOCUMENTS

| | | | | |
|---|---|---|---|---|
| 4,728,020 A * | 3/1988 | Green | | A61B 17/072 227/110 |
| 4,930,503 A * | 6/1990 | Pruitt | | A61B 17/072 227/178.1 |
| 5,395,030 A | 3/1995 | Kuramoto et al. | | |
| 5,470,008 A * | 11/1995 | Rodak | | A61B 17/072 227/176.1 |
| 5,655,398 A * | 8/1997 | Ginzburg | | B21B 13/023 72/241.4 |
| 5,833,695 A * | 11/1998 | Yoon | | A61B 17/072 606/139 |
| 6,241,140 B1 | 6/2001 | Adams et al. | | |
| 7,070,083 B2 * | 7/2006 | Jankowski | | A61B 17/072 227/176.1 |
| 8,070,038 B2 * | 12/2011 | Kostrzewski | | A61B 17/0682 227/180.1 |
| 8,627,994 B2 * | 1/2014 | Zemlok | | A61B 17/07207 227/176.1 |
| 8,789,739 B2 * | 7/2014 | Swensgard | | A61B 17/07207 227/177.1 |
| 8,955,732 B2 * | 2/2015 | Zemlok | | A61B 17/068 227/176.1 |
| 9,192,382 B2 * | 11/2015 | Kostrzewski | | A61B 17/115 |
| 9,375,218 B2 * | 6/2016 | Wheeler | | A61B 17/122 |
| 2002/0047036 A1 | 4/2002 | Sullivan et al. | | |
| 2010/0089973 A1 | 4/2010 | Kostrzewski | | |
| 2012/0012636 A1 | 1/2012 | Beckman et al. | | |
| 2012/0012638 A1 | 1/2012 | Huang et al. | | |
| 2012/0016413 A1 | 1/2012 | Timm et al. | | |
| 2012/0055973 A1 | 3/2012 | Kostrzewski | | |
| 2013/0105554 A1 | 5/2013 | Kostrzewski | | |
| 2016/0038145 A1 | 2/2016 | Kostrzewski | | |

FOREIGN PATENT DOCUMENTS

| | | |
|---|---|---|
| GB | 2038226 A | 7/1980 |
| JP | S55-78950 A | 6/1980 |
| JP | 3926831 B2 | 6/2007 |
| JP | 4091424 B2 | 5/2008 |
| JP | 2010-088882 A | 4/2010 |
| WO | WO 02/38037 A2 | 5/2002 |
| WO | WO 2012/009431 A2 | 1/2012 |

\* cited by examiner

STAPLER

CROSS-REFERENCE TO RELATED APPLICATIONS

This is a continuation of International Application PCT/JP2016/084074, with an international filing date of Nov. 17, 2016, which is hereby incorporated by reference herein in its entirety.

TECHNICAL FIELD

The present invention relates to a stapler.

BACKGROUND ART

In the related art, there is a known apparatus that performs a full-thickness excision of a tubular organ, wherein the apparatus performs suturing by sequentially pushing out a plurality of staple drivers (pushers) by means of a rotating cam and cuts out sutured tissue by means of a rotating blade (for example, see Publication of Japanese Patent No. 4091424).

With this apparatus, because staples are sequentially pushed out instead of all the staples being simultaneously pushed out, it is possible to reduce the amount of force required to perform suturing.

SUMMARY OF INVENTION

An aspect of the present invention is a stapler including: a holder provided with an accommodating portion that accommodates a plurality of staples with tips thereof, which pass through a suturing target, directed in one direction; a plurality of pushers that push out the staples accommodated in the accommodating portion in accordance with a plurality of groups thereof; an anvil that presses and deforms the staples pushed out from the accommodating portion by the pushers; driving-force transmitting mechanism that number are equal to or more to the plurality of groups, and that are respectively connected to the individual pushers, in which the movement thereof in directions other than the push-out directions of the individual pushers is restricted at the individual connection portions, and that transmit driving forces that move the individual pushers toward the anvil.

DESCRIPTION OF EMBODIMENT

A stapler 1 according to an embodiment of the present invention will be described below with reference to the drawings.

Figure 1:
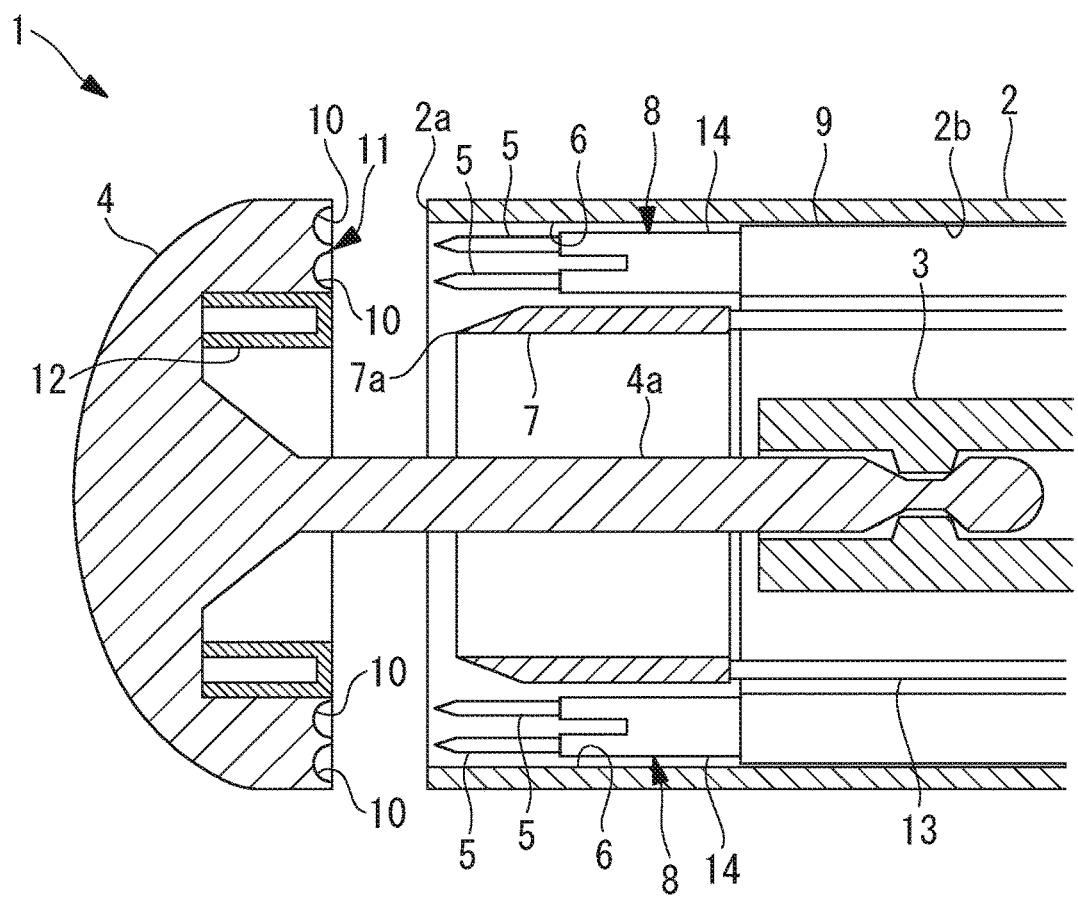
FIG. 1 is a longitudinal cross-sectional view of a distal-end portion, showing a stapler according to an embodiment of the present invention.
Figure 5:
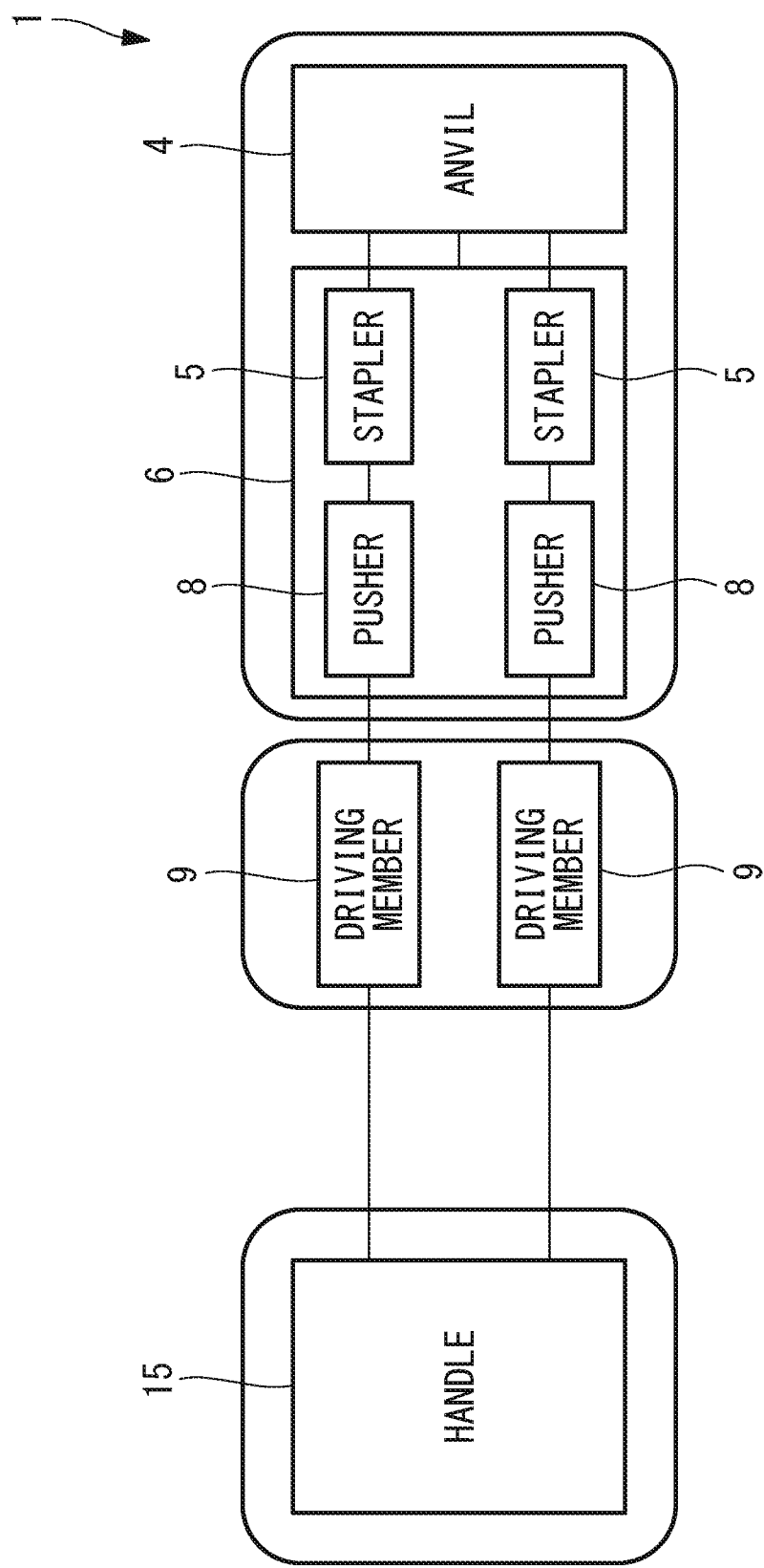
FIG. 5 is a schematic view showing the configuration of the stapler in FIG. 1.

As shown in FIGS. 1 and 5, the stapler 1 according to this embodiment is a circular-type medical stapler provided with: a cylindrical staple housing (holder) 2 having an annular distal-end surface (gripping surface) 2a; a center shaft 3 that is disposed in an axial direction by passing through the same center axis as a center hole 2b of the staple housing 2; an anvil 4 provided with a center rod 4a that is attached to a distal end of the center shaft 3 in an attachable/detachable manner; and a handle (driving portion) 15 with which the staple housing 2 is operated.

As a result of engaging the center rod 4a of the anvil 4 with the center shaft 3 and pulling the center shaft 3 toward a base end, it is possible to dispose the anvil 4 at a position at which a closed state in which the anvil 4 is brought into close contact with a distal-end surface 2a of the staple housing 2 is achieved.

The staple housing 2 is provided with: an annular staple cassette (accommodating portion) 6 that accommodates numerous staples 5, for example, by arraying the staples 5 in two rows in a circumferential direction over the entire circumference thereof; an annular cutter 7 that is disposed on an inner side of the staple cassette 6 in a radial direction over the entire circumference thereof; pushers 8 that eject the staples 5 accommodated in the staple cassette 6 toward the anvil 4 from the distal-end surface 2a; and driving members (driving-force transmitting mechanism) 9 that pushes out the pushers 8.

Figure 2:
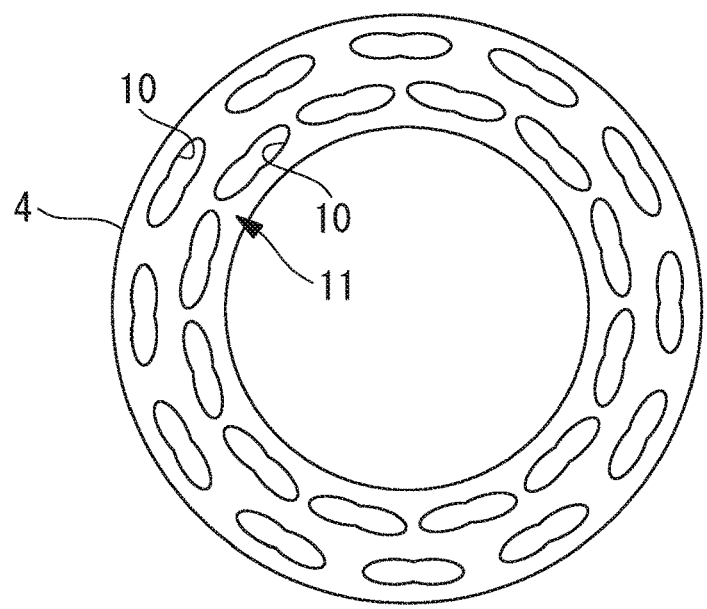
FIG. 2 is a front view of an example of an anvil provided in the stapler in FIG. 1.

As shown in FIG. 2, the anvil 4 is provided with: an annular anvil portion 11 provided with a plurality of anvil pockets 10 that are disposed at positions facing the directions (axial direction) in which the individual staples 5 in the staple housing 2 are ejected; and a receiving member 12 that is disposed, on an inner side of the anvil portion 11 in a radial direction, at a position facing a cutting edge 7a of the cutter 7 in the axial direction. A driving member 13 is also provided in the cutter 7 and is capable of pushing out the cutter 7 toward the receiving member 12.

Figure 4:
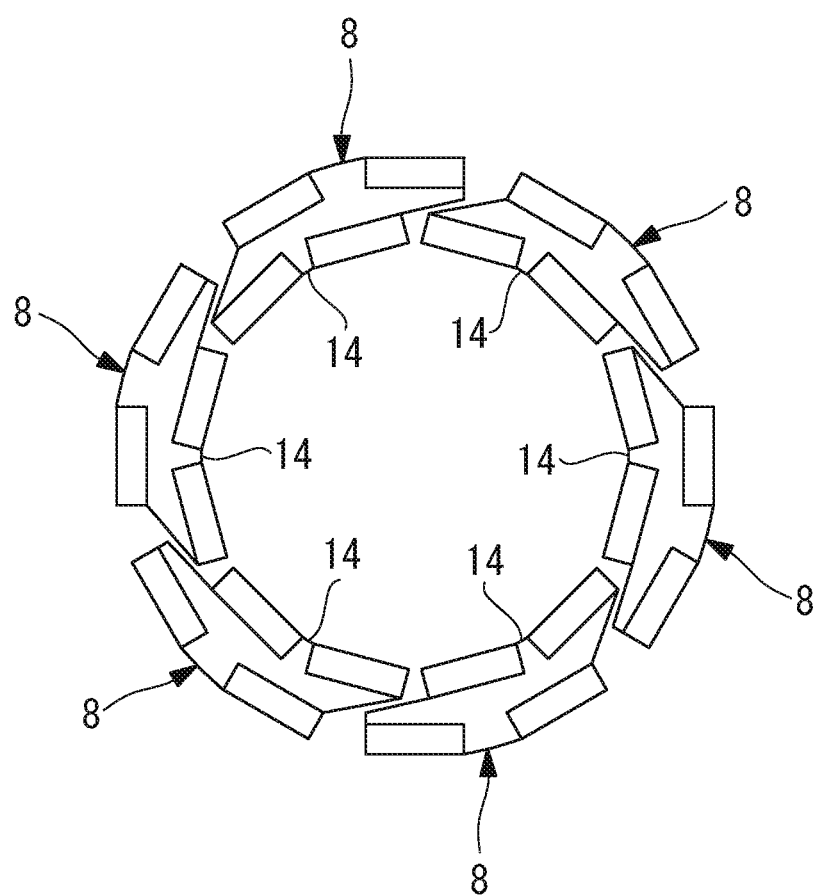
FIG. 4 is a front view showing examples of the pushers provided in the stapler in FIG. 1.

As shown in FIG. 4, in the stapler 1 according to this embodiment, as a result of the six pushers 8 being arrayed in the circumferential direction, the pushers 8 are arrayed in an annular form as a whole. The individual pushers 8 are provided with four pressing pieces 14 and are capable of simultaneously ejecting, by means of the four pressing pieces 14, a total of four staples 5 accommodated in the staple cassette 6, that is, two staples 5 on the inner circumferential side and two staples 5 on the outer circumferential side.

Figure 3A:
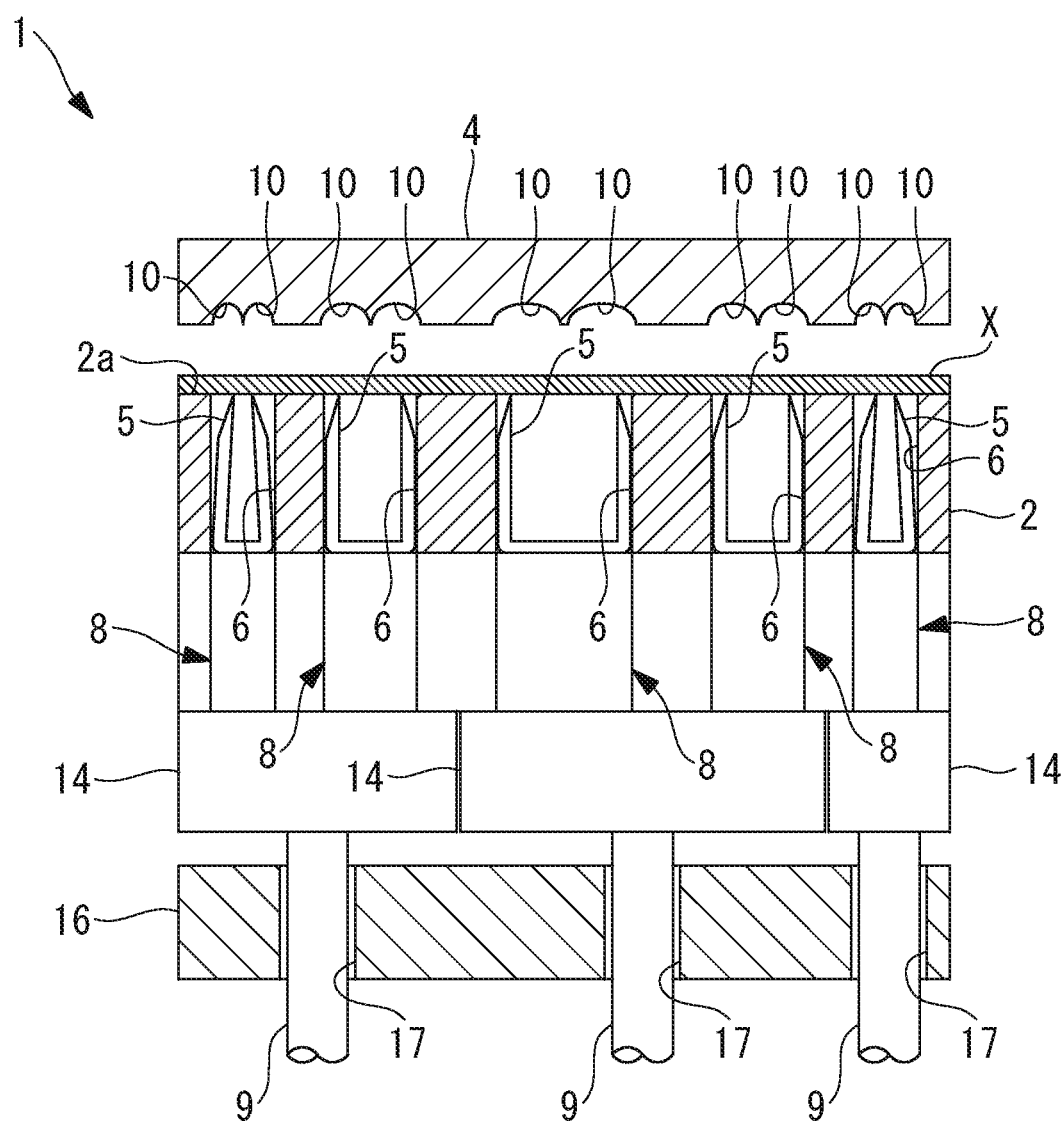
FIG. 3A is a side view of the distal-end portion of the stapler, showing a state before ejecting staples in the stapler in FIG. 1.
Figure 3B:
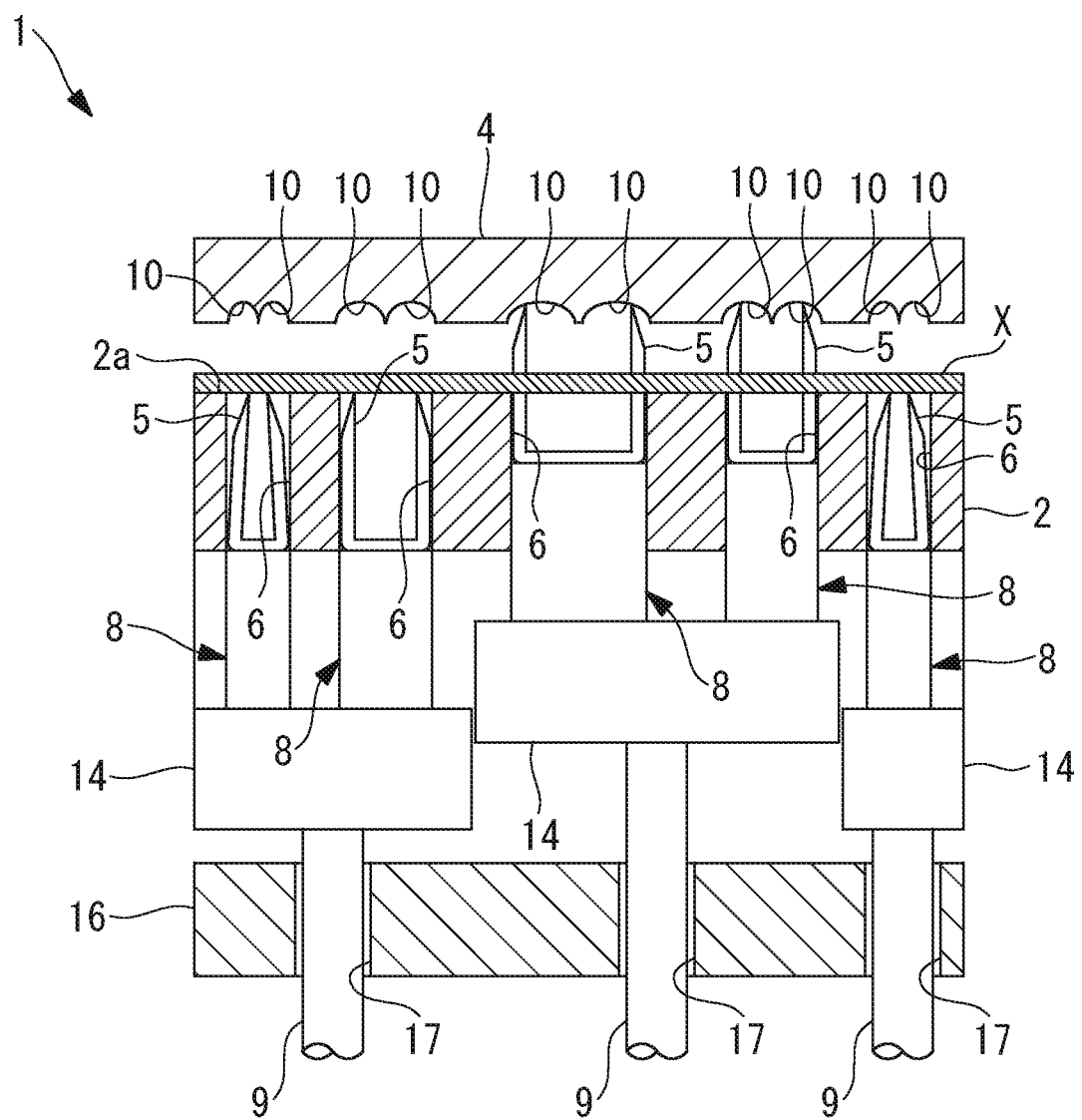
FIG. 3B is a side view of the distal-end portion of the stapler, showing a state in which the staples have been ejected by one pusher in the stapler in FIG. 1.

As shown in FIGS. 3A, 3B, and 4, driving members 9 are also connected, one each, to each of the pushers 8. The driving members 9 are, for example, wires that are connected, at distal ends thereof, to the pushers 8 and that are connected, at base ends thereof, to a handle 15 that generates a driving force. As shown in FIGS. 3A and 3B, as a result of the driving members 9 passing through, in the vicinity of connecting portions with the pushers 8, through-holes 17 of a support member 16 that is secured to the staple housing 2, the directions in which the driving members 9 are moved with respect to the staple housing 2 are restricted only to the directions that are parallel to the longitudinal axis of the staple housing 2, and the driving members 9 are restrained so as not to be moved in the directions that intersect to the longitudinal axis.

The handle 15 has a trigger (not shown) that is operated by being gripped by an operator. The trigger may be provided in the same number as the number of driving members 9, corresponding to the individual driving members 9, or switches for selecting the driving members 9 to which driving forces are supplied may be provided. A trigger is also connected to the base end of the driving member 13 connected to the cutter 7.

The operation of the stapler 1 according to this embodiment, thus configured, will be described below.

In order to suture and cut pieces of tissue (suturing target) X by using the stapler 1 according to this embodiment, first, the anvil 4 is inserted into one piece of the tubular tissue (tissue, suturing target) X to be sutured, and the tubular tissue X is folded toward the center rod 4a of the anvil 4. The staple housing 2 is inserted into another piece of the tubular tissue X to be sutured, and the tubular tissue X is folded toward the center shaft 3 of the staple housing 2. By doing so, the one piece of the tubular tissue X is disposed so as to cover the anvil portion 11 and the receiving member 12 of the anvil 4, and the other piece of the tubular tissue X is disposed so as to cover the distal-end surface 2a of the staple housing 2.

In this state, the center rod 4a of the anvil 4 is mounted to the center shaft 3 of the staple housing 2, and the closed state, in which the anvil 4 is brought close to the staple housing 2, is achieved by pulling the center shaft 3 toward the base end. By doing so, the tissue X is sandwiched between the staple housing 2 and the anvil 4.

Then, as shown in FIG. 3b, by operating the trigger of the handle 15, one of the driving members 9 is pushed out toward the distal end, which moves the pusher 8 connected to this driving member 9 toward the distal end, and the four staples 5 accommodated in the staple cassette 6 are ejected all at once by the four pressing pieces 14 of the pusher 8, thus causing the staples 5 to pass through the tissue X with needle tips thereof.

The staples 5 that have passed through the tissue X are bent and deformed by the anvil pockets 10 provided in the anvil 4 so that the needle tips thereof are folded back, and, as a result, it is possible to suture the tissue X in that portion. By sequentially operating the triggers, the operator moves, one by one, the pushers 8 toward the distal end, and sutures the tissue X.

In this case, with this embodiment, because the staples 5 in portions in the circumferential direction are pushed out by pushing out, one by one, the plurality of pushers 8 that are provided as separate pieces in the circumferential direction instead of simultaneously ejecting all of the staples 5 disposed over the entire circumference, it is possible to reduce the amount of force that the operator applies when operating the triggers, and thus, there is an advantage in that it is possible to reduce the burden on the operator.

In this case, the driving members 9 are respectively connected to the individual pushers 8, and, in the vicinity of the portions in which the pushers 8 and the driving members 9 are connected, the directions in which the driving members 9 are moved are restricted only to the longitudinal axial direction; therefore, pressing forces do not act in the directions that intersect the directions in which the staples 5 are ejected by the pushers 8, and thus, it is possible to prevent the occurrence of displacement. In other words, it is possible to eject the staples 5 straight toward the anvil 4, and thus, there is an advantage in that it is possible to stably perform suturing.

Figure 6:
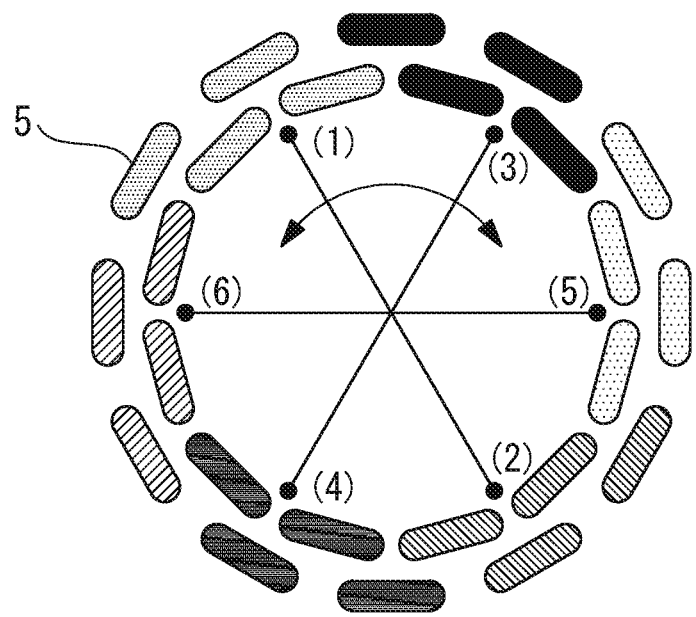
FIG. 6 is a front view for explaining the order in which the staplers in the stapler in FIG. 1 are ejected.

As shown in FIGS. 3A and 3B, as a result of sequentially pushing out the plurality of pushers 8, which are arrayed in the circumferential direction, along one direction in the circumferential direction, there is an advantage in that it is possible to perform suturing while allowing a liquid or a gas contained in the tissue X, such as a flow of blood, to escape so as not to trap such a liquid or a gas therein. As a result of sequentially pushing out the pairs of pushers 8 that are disposed at opposing positions in the radial directions in accordance with the numbers (1) to (6) indicated in FIG. 6, there is an advantage in that it is possible to evenly perform suturing in the circumferential direction even if the tissue X is easily stretchable tissue.

Then, after pushing out all of the pushers 8 and completing suturing of the tissue X, the trigger (not shown) is operated and the cutter 7 is moved toward the distal end. By doing so, by sandwiching the tissue X between the cutting edge 7a of the cutter 7 and the receiving member 12 of the anvil 4 at a portion on an inner side of the tissue X in the radial direction in the state in which the tissue X is sutured by the staples 5 and by moving the cutter 7 forward until reaching a position at which the receiving member 12 is passed through, the tissue X is circularly cut with the cutter 7. As a result of such motions, the tissue X is sutured and cut.

In this embodiment, although wires have been described as examples of the driving members 9, rigid shafts may be employed. Although the case in which the six pushers 8 are arrayed in the circumferential direction has been described as an example, there is no limitation thereto, and the number of pushers 8 may be an arbitrary number equal to or greater than two.

Figure 7:
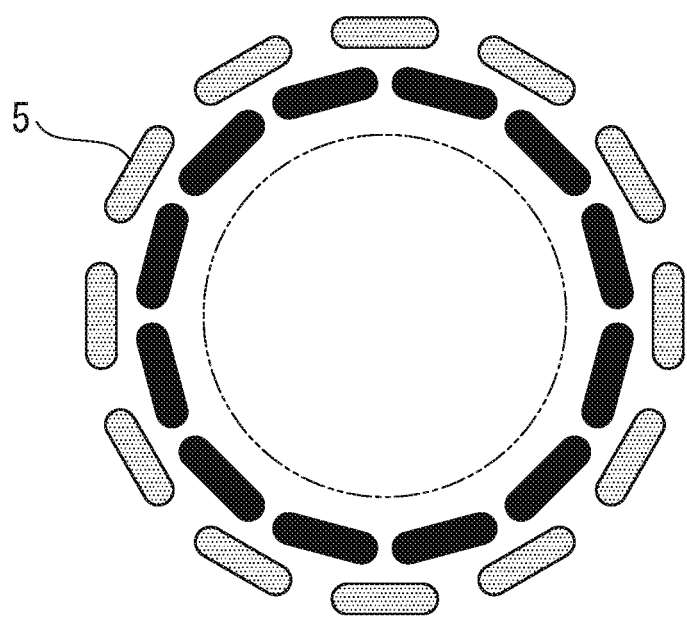
FIG. 7 is a front view showing groups of staplers in a modification of the stapler in FIG. 1.
Figure 8:
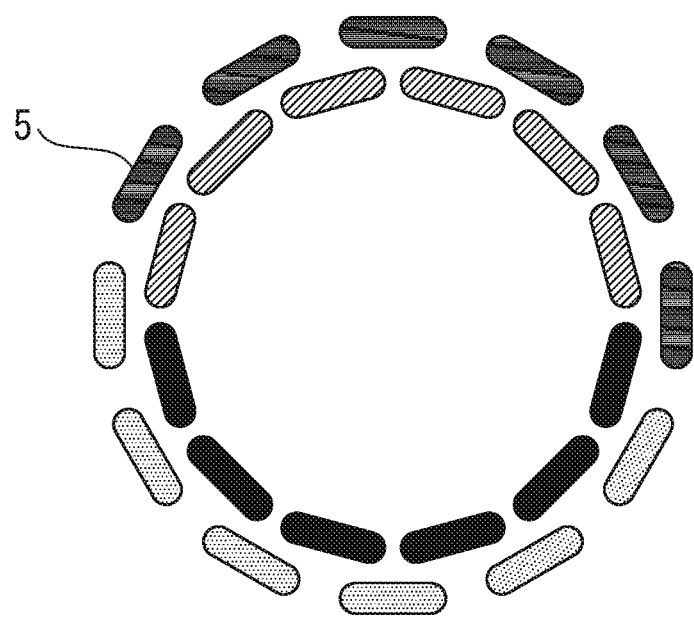
FIG. 8 is a front view showing groups of staplers in another modification of the stapler in FIG. 1.

An example in which the plurality of pushers 8 are provided in the circumferential direction has been described; however, alternatively, as shown in FIG. 7, pushers 8 that are separated in the radial direction may be employed so that the staples 5 that are divided into groups are ejected in accordance with the grouping, or, as shown in FIG. 8, pushers 8 that are separated both in the radial direction and the circumferential direction may be employed so that the staples 5 that are divided into groups are ejected in accordance with the grouping.

In the case in which the pushers 8 separated in the radial direction are employed, by performing suturing on an inner side in the radial direction after performing suturing on an outer side in the radial direction, there is an advantage in that it is possible to perform suturing while allowing a liquid or a gas contained in the tissue X, such as a flow of blood, to escape toward the surface that is cut and separated so as not to trap such a liquid or a gas therein.

By performing suturing on the outer side in the radial direction after performing suturing on the inner side in the radial direction, there is an advantage in that it is possible to perform suturing while reducing bleeding.

Figure 9:
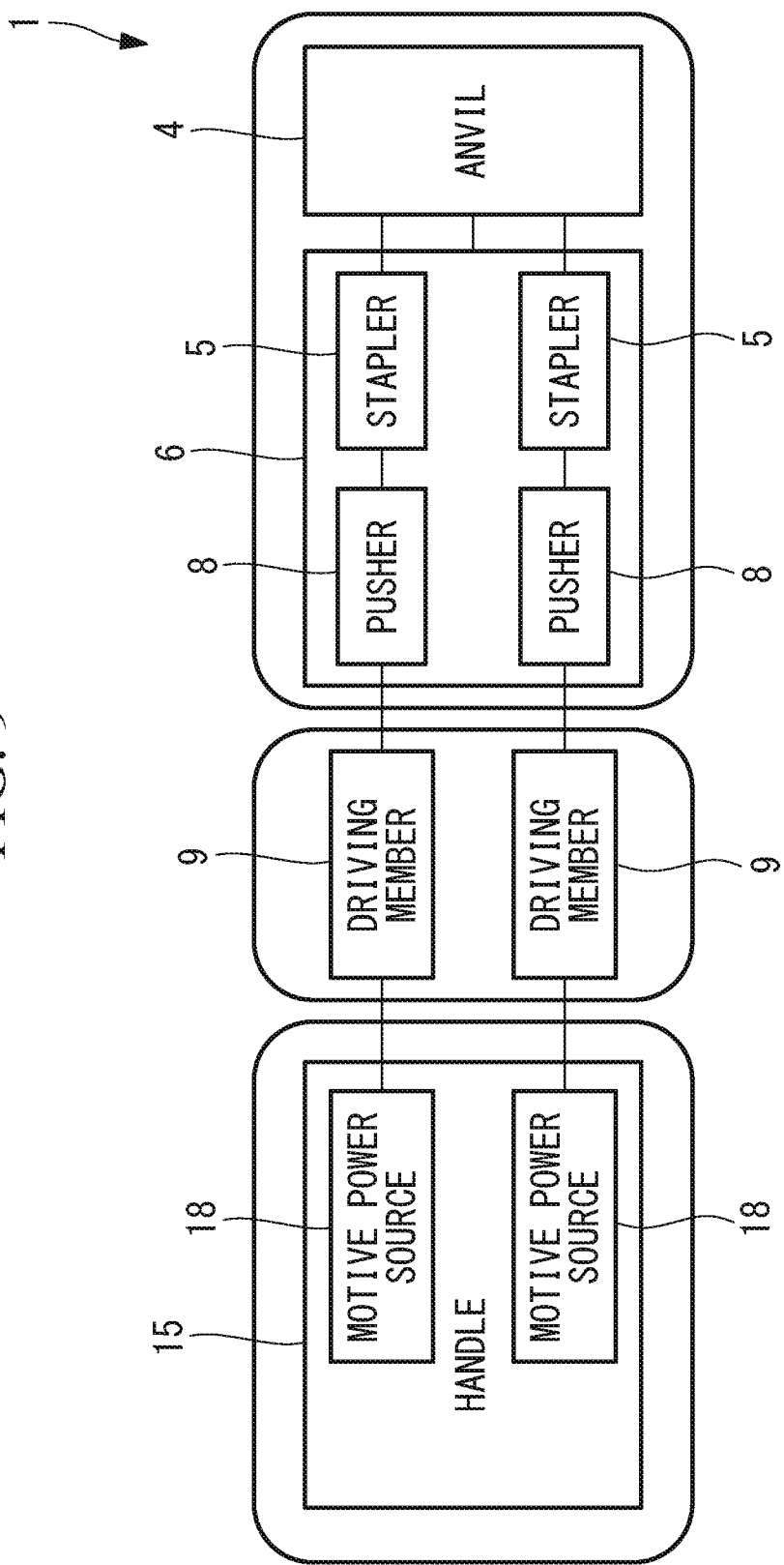
FIG. 9 is a schematic view showing the configuration of the modification of the stapler in FIG. 1.

In this embodiment, the forces that the operator applies to the triggers provided in the handle 15 are transmitted to the pushers 8 by the driving members 9, thus the staples 5 are manually ejected; however, alternatively, as shown in FIG. 9, motive power sources 18 that generate driving forces in accordance with the amounts by which the triggers of the handle 15 are operated by the operator may be respectively provided in the driving members 9.

Figure 10:
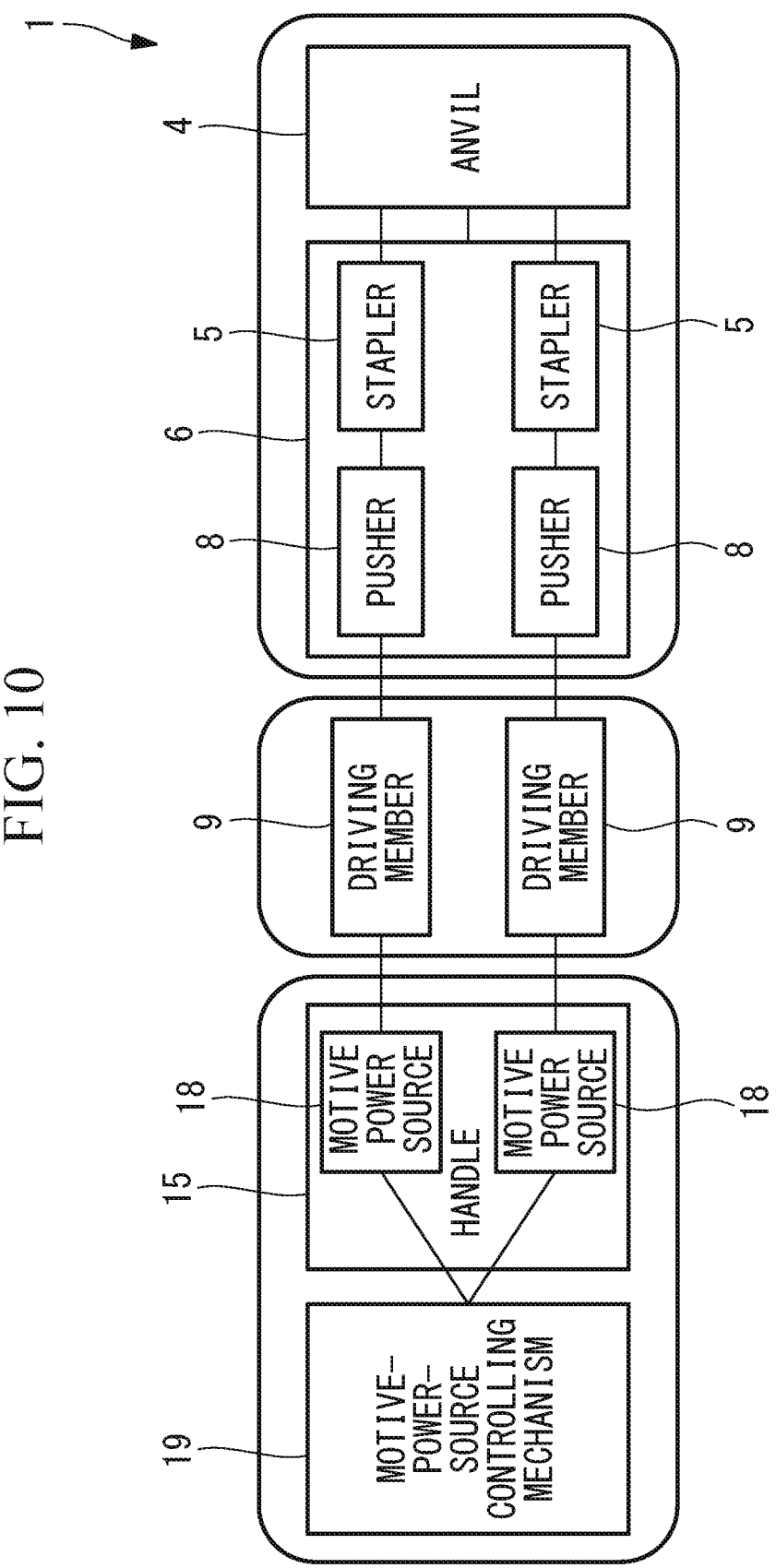
FIG. 10 is a schematic view showing the configuration of the other modification of the stapler in FIG. 1.

As shown in FIG. 10, a motive-power-source controlling mechanism (control portion) 19 that controls the plurality of motive power sources 18 may be provided, and, by selecting one of the pushers 8 in accordance with the operation input by the operator, such as a button operation, the motive power may be generated in the corresponding motive power source 18.

Figure 11:
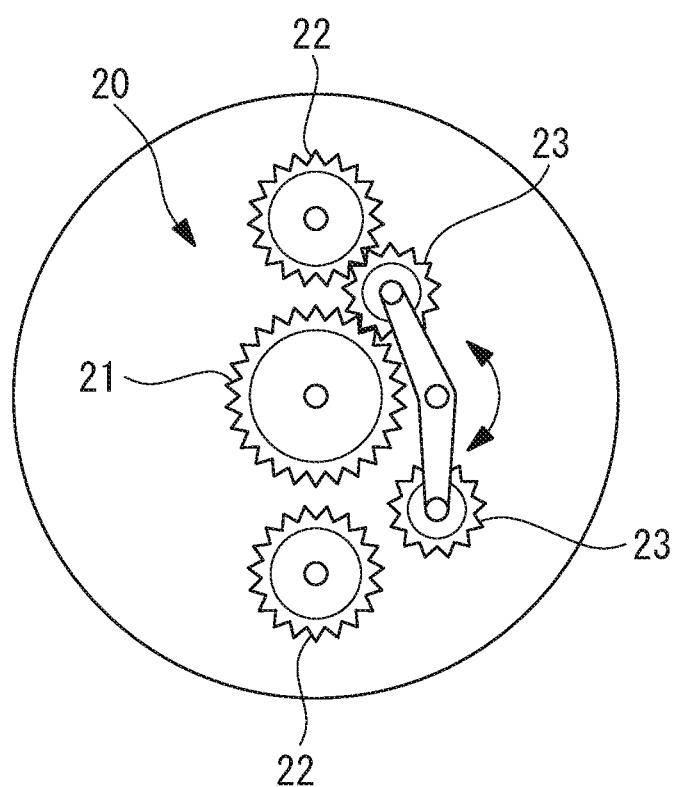
FIG. 11 is a front view for explaining a switching mechanism in the other modification of the stapler in FIG. 1.
Figure 12:
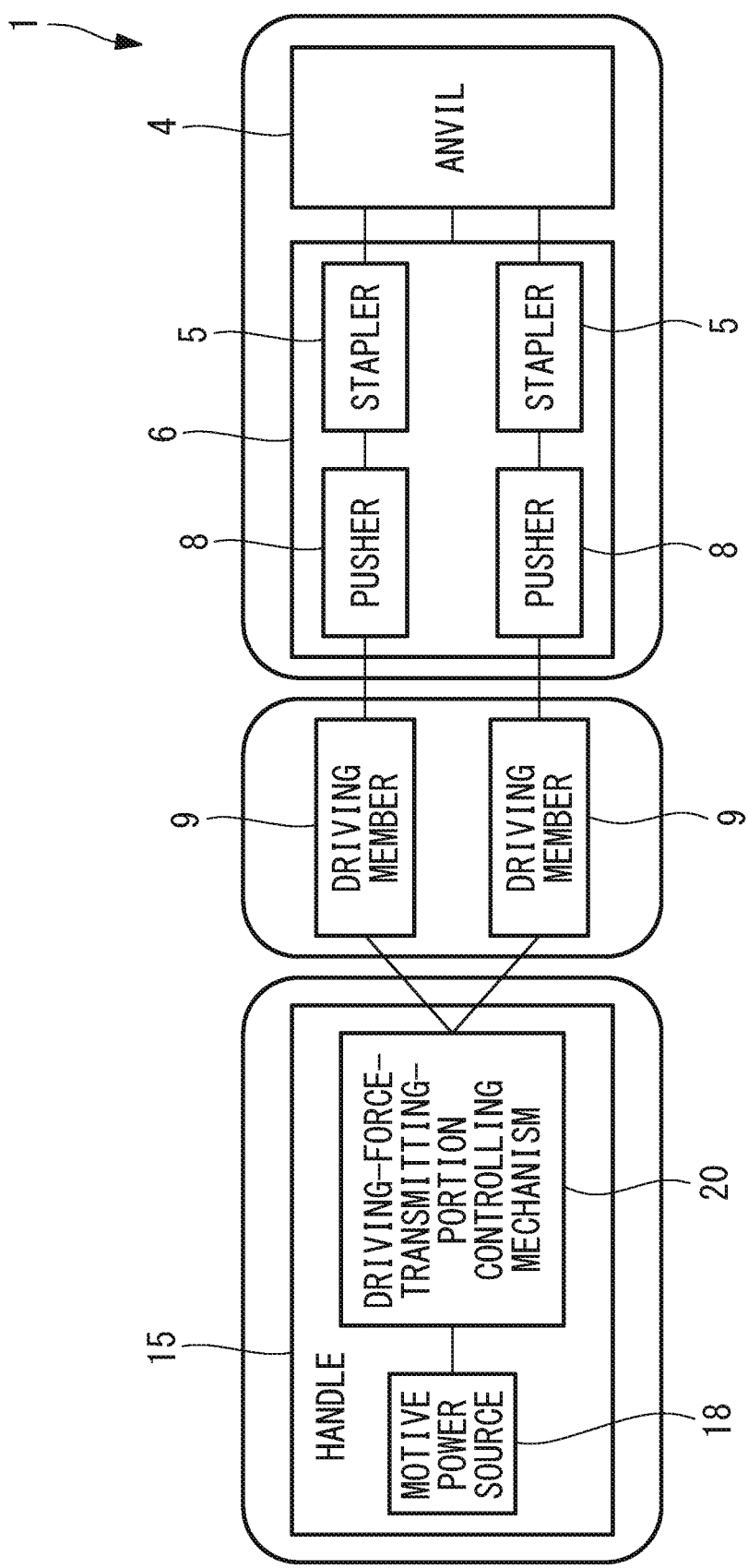
FIG. 12 is a schematic view showing the configuration of the stapler in FIG. 10.

As shown in FIGS. 11 and 12, the plurality of driving members 9 may be associated with a single motive power source 18, and a driving-force-transmitting-mechanism controlling mechanism 20 that switches connections therebetween so that the motive power source 18 is connected to the driving member 9 corresponding to the selected pusher 8 may be provided. In the example shown in FIG. 11, between a driving gear 21 that is attached to a motor, which is the motive power source 18, and two driven gears 22 that are attached to the individual driving members 9, two movable gears 23 that individually engage with the driving gear 21 and the driven gears 22 are provided, and the engagement is switched so that one of the movable gears 23 is engaged between the driving gear 21 and the driven gears 22, and, consequently, it is possible to supply the driving force from the motive power source 18 only to one of the driving members 9.

Figure 13:
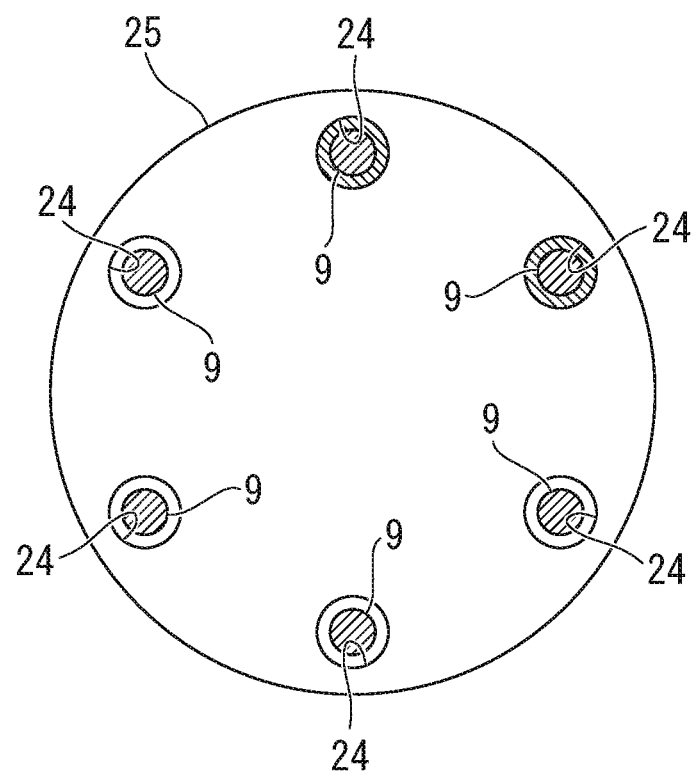
FIG. 13 is a front view for explaining a clutch mechanism in the other modification of the stapler in FIG. 1.

As shown in FIG. 13, a clutch mechanism 25 may be provided at an intermediate position in the longitudinal direction of the driving members 9. As the clutch mechanism 25, a member that is provided with through-holes 24 through which the individual driving members 9 respectively pass and that fasten the individual through-holes 24 around the driving members 9 by decreasing the hole sizes may be employed.

By doing so, in the case in which the plurality of pushers 8 need to be simultaneously moved, by operating the clutch mechanism 25 and by contracting the through-holes 24 through which the driving members 9 corresponding to the pushers 8 to be moved pass, it is possible to simultaneously push out, with the driving force applied to one driving member 9, the two pushers 8 connected to the plurality of (in the example shown in FIG. 13, two indicated by diagonal lines between the driving members 9 and the through-holes 24) driving members 9.

By doing so, in addition to the case in which all of the pushers 8 are respectively pushed out, it is possible to simultaneously push out two or more of the pushers 8, and it is possible to adjust the timing at which the staples 5 are ejected.

As a result, the following aspects are derived from the above-described embodiments.

An aspect of the present invention is a stapler including: a holder provided with an accommodating portion that accommodates a plurality of staples with tips thereof, which pass through a suturing target, directed in one direction; a plurality of pushers that push out the staples accommodated in the accommodating portion in accordance with a plurality of groups thereof; an anvil that presses and deforms the staples pushed out from the accommodating portion by the pushers; driving-force transmitting mechanism that number are equal to or more to the plurality of groups, and that are respectively connected to the individual pushers, in which the movement thereof in directions other than the push-out directions of the individual pushers is restricted at the individual connection portions, and that transmit driving forces that move the individual pushers toward the anvil; and a driving portion that is configured to generate the driving forces transmitted by the driving-force transmitting mechanism.

With this aspect, when the driving portion is activated, the driving forces generated by the driving portion are transmitted to the pushers by the driving-force transmitting mechanism, and the staples corresponding to the pushers are pushed out from the accommodating portion of the holder, and, as a result, after the sharp tips of the staples pass through the suturing target, the staples are pressed against the anvil and deformed, thus suturing the suturing target. In this case, because the plurality of staples are divided into the plurality of groups and are pushed out by separate pushers in accordance with the grouping, the driving forces transmitted by driving-force transmitting mechanism to push out the individual pushers, in other words, the driving forces generated by the driving portion may be less than the driving forces for pushing out all of the staples all at once, and thus, it is possible to perform suturing work in a simple manner.

Also, in this case, because, at the connecting portions to the pushers, the movements of the driving-force transmitting mechanism other than those in the directions in which the staples are pushed out are restricted, the driving forces transmitted by the driving-force transmitting mechanism are prevented from acting in the directions that intersect the push-out directions of the pushers, and thus, it is possible to prevent the pushers from being displaced.

In the above-described aspect, the individual pushers may push out the staples in accordance with a plurality of groups into which the staples are divided in a circumferential direction.

By doing so, it is possible to set the order in which the suturing target is sutured with the staples in the circumferential direction. By sequentially suturing in one direction in the circumferential direction, in the case in which the suturing target contains a body fluid or a gas, such as a flow of blood, it is possible to perform suturing while allowing these substances to escape. In addition, by prioritizing suturing opposing of positions on either side of the center, it is possible to prevent the suturing target from escaping, and it is possible to evenly suture the suturing target.

In addition, in the above-described aspect, the individual pushers may push out the staples in accordance with a plurality of groups into which the staples are divided in a radial direction.

By doing so, it is possible to set the order in which the suturing target is sutured with the staples, in the radial direction, from an inner side to an outer side or from an outer side to an inner side.

As a result of suturing the inner side after suturing an outer side in the radial direction, in the case in which the suturing target contains a body fluid or a gas, such as a flow of blood, it is possible to possible to perform suturing while allowing these substances to escape toward the side to be cut and separated. In addition, by suturing the outer side after suturing the inner side, it is possible to reduce bleeding.

In addition, suturing may be executed by switching the suturing order between the circumferential direction and the radial direction.

In addition, in the above-described aspect, the driving portion may manually generate the driving forces.

By doing so, although the driving force is generated by the manual operation by the operator, because the required amount of driving force is reduced by dividing the pushers, the amount of force the operator applies is reduced, and it is possible to reduce the burden on the operator.

In addition, in the above-described aspect, the driving portion may be provided with a motive power source that is configured to generate the driving forces.

By doing so, the amount of force required to eject the staples in the individual groups is sufficiently reduced as compared with the amount of driving force required to eject all of the staples, and thus, it is possible to reliably eject the staples even if the driving force is attenuated in the process of being transmitted by the driving-force transmitting mechanism.

In addition, in the above-described aspect, the driving portion may be provided with a control portion that is configured to control the driving forces to be transmitted by the driving-force transmitting mechanism so as to move the individual pushers at a predetermined timing.

By doing so, the driving force transmitted by the driving-force transmitting mechanism is controlled so that the control portion causes the individual pushers to be moved at a predetermined timing, and it is possible to simplify the operation by the operator.

REFERENCE SIGNS LIST 1 stapler
2 staple housing (holder)
4 anvil
5 staple
6 staple cassette (accommodating portion)
8 pusher
9 driving member (driving-force transmitting mechanism)
15 handle (driving portion)
18 motive power source
19 motive-power-source controlling mechanism (control portion)
X tissue (suturing target)

The invention claimed is:

1. A stapler comprising:
    a holder provided with an accommodating portion, the accommodating portion accommodating a plurality of staples, each of the plurality of staples having one or more tips extended in a first direction, each of the one or more tips being configured to pass through a suturing target;
    a plurality of pushers each configured to push out one or more staples of the plurality of staples, the one or more staples being less than all of the plurality of staples accommodated in the accommodating portion;
    an anvil that presses and deforms the plurality of staples pushed out from the accommodating portion by the plurality of pushers; and
    a plurality of driving-force transmitting mechanisms connected to a respective one of the plurality of pushers, wherein each of the plurality of driving-force transmitting mechanisms are movable in the first direction to each individually transmit a driving force that moves the respective one of the plurality of pushers toward the anvil independently of other ones of the plurality of pushers.

2. The stapler according to claim 1, wherein each of the plurality of pushers push out the one or more staples in accordance with a plurality of groups into which the plurality of staples are divided in a circumferential direction.

3. The stapler according to claim 1, wherein each of the plurality of pushers push out the one or more staples in accordance with a plurality of groups into which the plurality of staples are divided in a radial direction.

4. The stapler according to claim 1, wherein each of the plurality of driving-force transmitting mechanisms manually generate the driving force.

5. The stapler according to claim 1, wherein each of the plurality of driving-force transmitting mechanisms is provided with a motive power source configured to generate the driving force.

6. The stapler according to claim 1, wherein each of the plurality of driving-force transmitting mechanisms is provided with a control portion configured to control the driving force so as to move the respective one of the plurality of pushers at a predetermined timing.

7. The stapler according to claim 1, wherein each of the plurality of pushers are oriented to extend in the first direction.

8. The stapler according to claim 1, wherein each of the plurality of driving-force transmitting mechanisms are oriented to extend in the first direction.

9. The stapler according to claim 1, further comprising a handle having a plurality of actuation members for individually actuating each of the plurality of driving-force transmitting mechanisms, respectively.

10. The stapler according to claim 1, further comprising a support member having a hole corresponding to each of the driving-force transmitting mechanisms for restricting the movement of each of the driving-force transmitting mechanisms in directions offset from the first direction.

11. A stapler comprising:
    a holder provided with an accommodating portion, the accommodating portion accommodating a plurality of staples, each of the plurality of staples having one or more tips extended in a first direction, each of the one or more tips being configured to pass through a suturing target;
    a first pusher configured to push out a first group of one or more staples of the plurality of staples, the first group being less than all of the plurality of staples accommodated in the accommodating portion;
    a second pusher configured to push out a second group of one or more staples of the plurality of staples, the second group being less than all of the plurality of staples accommodated in the accommodating portion;
    an anvil that presses and deforms the plurality of staples pushed out from the accommodating portion by the first and second pushers; and
    a first driving-force transmitting mechanism connected to the first pusher, wherein the first driving-force transmitting mechanism is movable in the first direction to transmit a first driving force that moves the first pusher toward the anvil; and
    a second driving-force transmitting mechanism connected to the second pusher, wherein the second driving-force transmitting mechanism is movable in the first direction to transmit a second driving force that moves the second pusher toward the anvil independently of the first pusher.

12. A stapler according to claim 11, wherein the first and second groups of the plurality of staples are divided in a circumferential direction.

13. A stapler according to claim 11, wherein the first and second groups of the plurality of staples are divided in a radial direction.

14. A stapler according to claim 11, wherein one or more of the first and second driving-force transmitting mechanisms manually generate the respective first and second driving force.

15. A stapler according to claim 11, wherein one or more of the first and second driving-force transmitting mechanisms is provided with a motive power source configured to generate the respective first and second driving force.

16. A stapler according to claim 11, wherein one or more of the first and second driving-force transmitting mechanisms is provided with a control portion configured to control the respective first and second driving force so as to move the respective first and second pushers at a predetermined timing.

17. The stapler according to claim 11, wherein each of the plurality of pushers are oriented to extend in the first direction.

18. The stapler according to claim 11, wherein each of the plurality of driving-force transmitting mechanisms are oriented to extend in the first direction.

19. The stapler according to claim 11, further comprising a handle having a plurality of actuation members for individually actuating each of the plurality of driving-force transmitting mechanisms, respectively.

20. The stapler according to claim 11, further comprising a support member having a hole corresponding to each of the first and second driving-force transmitting mechanisms for restricting the movement of each of the first and second driving-force transmitting mechanisms in directions offset from the first direction.

* * * * *